United States Patent
Spiridigliozzi et al.

(10) Patent No.: US 7,588,596 B2
(45) Date of Patent: Sep. 15, 2009

(54) ENDOLUMINAL PROSTHESIS ADAPTED TO RESIST MIGRATION AND METHOD OF DEPLOYING THE SAME

(75) Inventors: John Spiridigliozzi, Sharon, MA (US); Ilya Yampolski, West Roxbury, MA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 216 days.

(21) Appl. No.: 11/025,020

(22) Filed: Dec. 29, 2004

(65) Prior Publication Data

US 2006/0142835 A1 Jun. 29, 2006

(51) Int. Cl.
 *A61F 2/06* (2006.01)
(52) U.S. Cl. ..................... 623/1.16; 623/1.35
(58) Field of Classification Search ................ 623/1.16, 623/1.35, 1.12
 See application file for complete search history.

(56) References Cited

U.S. PATENT DOCUMENTS

| | | | |
|---|---|---|---|
| 4,140,126 A | 2/1979 | Choudhury | |
| 4,776,337 A | 10/1988 | Palmaz | |
| 5,609,627 A | 3/1997 | Goicoechea et al. | |
| 5,716,365 A | 2/1998 | Goicoechea et al. | |
| 5,749,918 A | 5/1998 | Hogendijk et al. | |
| 5,782,906 A | 7/1998 | Marshall et al. | |
| 5,800,521 A | 9/1998 | Orth | |
| 5,800,526 A | 9/1998 | Anderson et al. | |
| 5,868,783 A * | 2/1999 | Tower | 606/198 |
| 5,871,537 A | 2/1999 | Holman et al. | |
| 5,938,696 A | 8/1999 | Goicoechea et al. | |
| 6,015,431 A | 1/2000 | Thornton et al. | |
| 6,033,434 A * | 3/2000 | Borghi | 623/1.35 |
| 6,056,775 A * | 5/2000 | Borghi et al. | 623/1.16 |
| 6,096,073 A | 8/2000 | Webster et al. | |
| 6,117,167 A | 9/2000 | Goicoechea et al. | |
| 6,168,621 B1 | 1/2001 | Vrba | |
| 6,183,509 B1 * | 2/2001 | Dibie | 623/1.35 |
| 6,319,278 B1 * | 11/2001 | Quinn | 623/1.13 |
| 6,409,757 B1 | 6/2002 | Trout, III et al. | |
| 6,464,721 B1 | 10/2002 | Marcade et al. | |

(Continued)

FOREIGN PATENT DOCUMENTS

WO WO 00/76423 12/2000

(Continued)

OTHER PUBLICATIONS

EPO Communication pursuant to Article 94(3) EPC for European Application No. 05 853 433.0-2320 mailed Jan. 13, 2009.

(Continued)

*Primary Examiner*—Corrine McDermott
*Assistant Examiner*—Cheryl Miller
(74) *Attorney, Agent, or Firm*—Brooks, Cameron & Huebsch, PLLC

(57) ABSTRACT

An endoluminal prosthesis for treatment of a condition in a lumen in the vicinity of a branch lumen, the lumen being adapted to resist migration, is provided. In one embodiment, the prosthesis includes a substantially tubular main stent adapted for placement in the main lumen. A substantially tubular anchor stent is connected to the main stent and adapted for placement in the branch lumen.

15 Claims, 10 Drawing Sheets

U.S. PATENT DOCUMENTS

| | | | |
|---|---|---|---|
| 6,517,572 B2 | 2/2003 | Kugler et al. | |
| 6,551,350 B1 | 4/2003 | Thornton et al. | |
| 6,585,758 B1 | 7/2003 | Chouinard et al. | |
| 6,599,302 B2 | 7/2003 | Houser et al. | |
| 6,669,720 B1 * | 12/2003 | Pierce | 623/1.13 |
| 6,773,453 B2 | 8/2004 | Ravenscroft | |
| 7,147,661 B2 * | 12/2006 | Chobotov et al. | 623/1.16 |
| 7,169,177 B2 * | 1/2007 | Obara | 623/1.35 |
| 2002/0058993 A1 | 5/2002 | Landau et al. | |
| 2003/0120331 A1 | 6/2003 | Chobotov et al. | |
| 2003/0199967 A1 | 10/2003 | Hartley et al. | |
| 2003/0236570 A1 | 12/2003 | Cook et al. | |
| 2004/0138736 A1 | 7/2004 | Obara | |
| 2006/0030932 A1 * | 2/2006 | Kantor et al. | 623/1.16 |
| 2006/0089704 A1 * | 4/2006 | Douglas | 623/1.12 |
| 2006/0271164 A1 * | 11/2006 | Shaolian et al. | 623/1.16 |

FOREIGN PATENT DOCUMENTS

WO    WO 2004/000169    12/2003

OTHER PUBLICATIONS

International Search Report for International Application No. PCT/US2005/044506 mailed on Mar. 29, 2006.

* cited by examiner

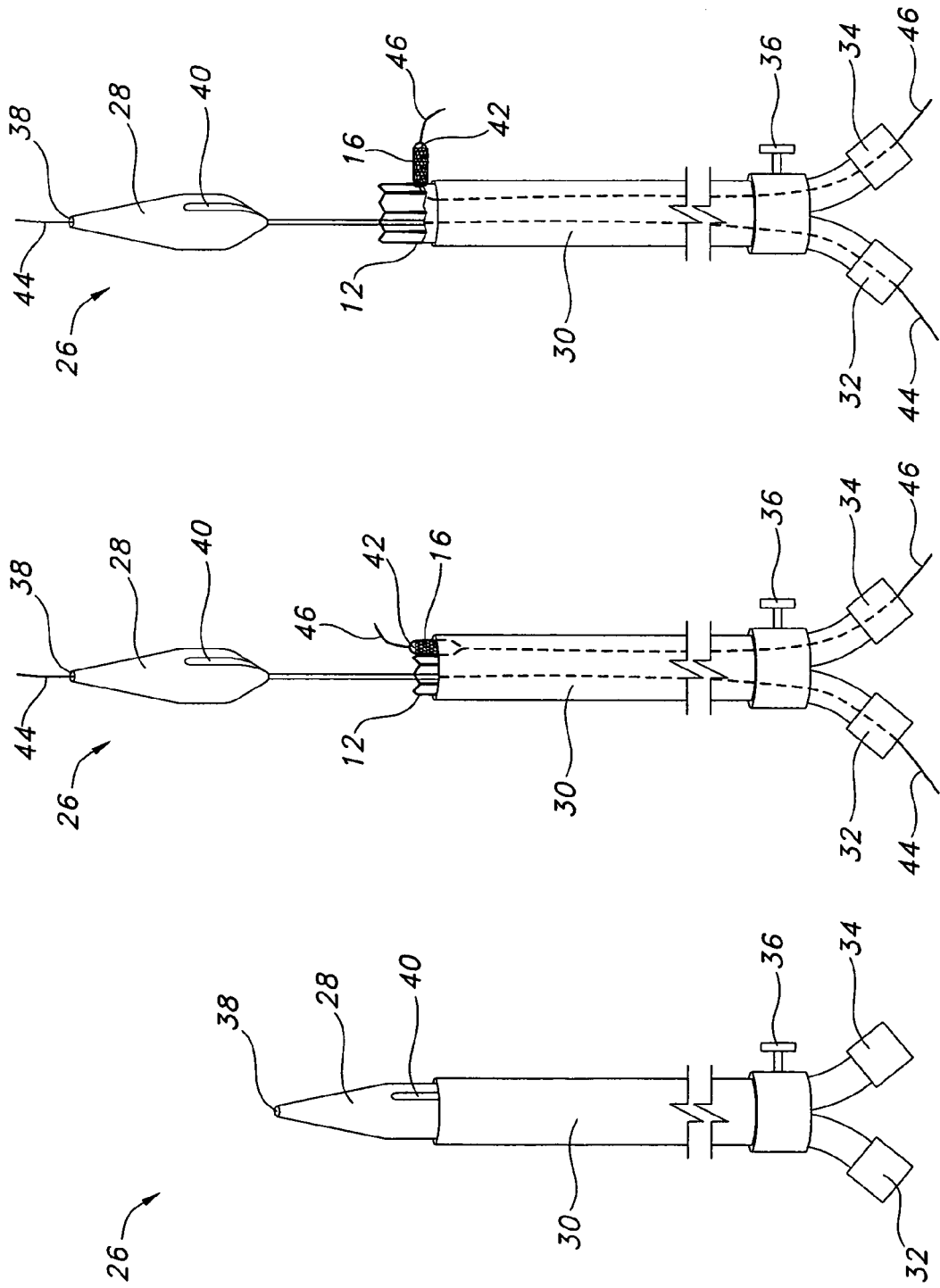

US 7,588,596 B2

ENDOLUMINAL PROSTHESIS ADAPTED TO RESIST MIGRATION AND METHOD OF DEPLOYING THE SAME

BACKGROUND OF THE INVENTION

Endoluminal graft prostheses adapted to be placed in a lumen in the vicinity of a branch lumen are typically used, for example, in the treatment of abdominal aortic aneurysms (AAAs). Once placed, such prostheses may experience changing lumen morphology. More specifically, a prosthesis deployed for treatment of an AAA may be subjected to downward forces, thereby causing the prosthesis to migrate distally (away from the heart).

Accordingly, there remains a need for a prosthesis suitable for placement in a lumen, in the vicinity of a branch lumen, that improves fixation and resists migration.

SUMMARY OF THE INVENTION

An endoluminal prosthesis for treatment of a condition in a body lumen near a branch lumen is adapted to resist migration. In one embodiment, the prosthesis includes a substantially tubular self-expandable main stent adapted for placement in the main lumen, or the aorta in the case of a device for treatment of an AAA. A substantially tubular anchor stent is pivotally connected to the main stent and adapted for placement in the branch lumen, or a renal artery in the case of an AAA device.

BRIEF DESCRIPTION OF THE DRAWINGS

FIG. 4A is a representation of a delivery device comprised of a tip and a sheath for deployment of the endovascular prosthesis illustrated in FIG. 1;

FIG. 4B shows the delivery device illustrated in FIG. 4A during an early stage of deployment with the anchor stent in a pre-deployment configuration;

FIG. 4C shows the delivery device illustrated in FIG. 4A during a later stage of deployment with the anchor stent in a post-deployment configuration;

DETAILED DESCRIPTION OF THE INVENTION

Although the invention is illustrated and described herein with reference to specific embodiments, the invention is not intended to be limited to the details shown. Rather, various modifications may be made in the details within the scope and range of equivalents of the claims and without departing from the invention.

Referring generally to FIGS. 1-3 and 8B, there is shown an embodiment of an endovascular prosthesis 10 for treatment of an abdominal aortic aneurysm (AAA) "A," wherein the prosthesis 10 is adapted to resist migration. Prosthesis 10 includes a substantially tubular, self-expandable, bifurcated main stent 12 adapted for placement below the renal arteries "R," the main stent 12 having a graft 14 (not shown in FIGS. 1 and 3). A substantially tubular anchor stent 16 is pivotally connected to main stent 12 and adapted for placement in a renal artery "R."

Figure 1:
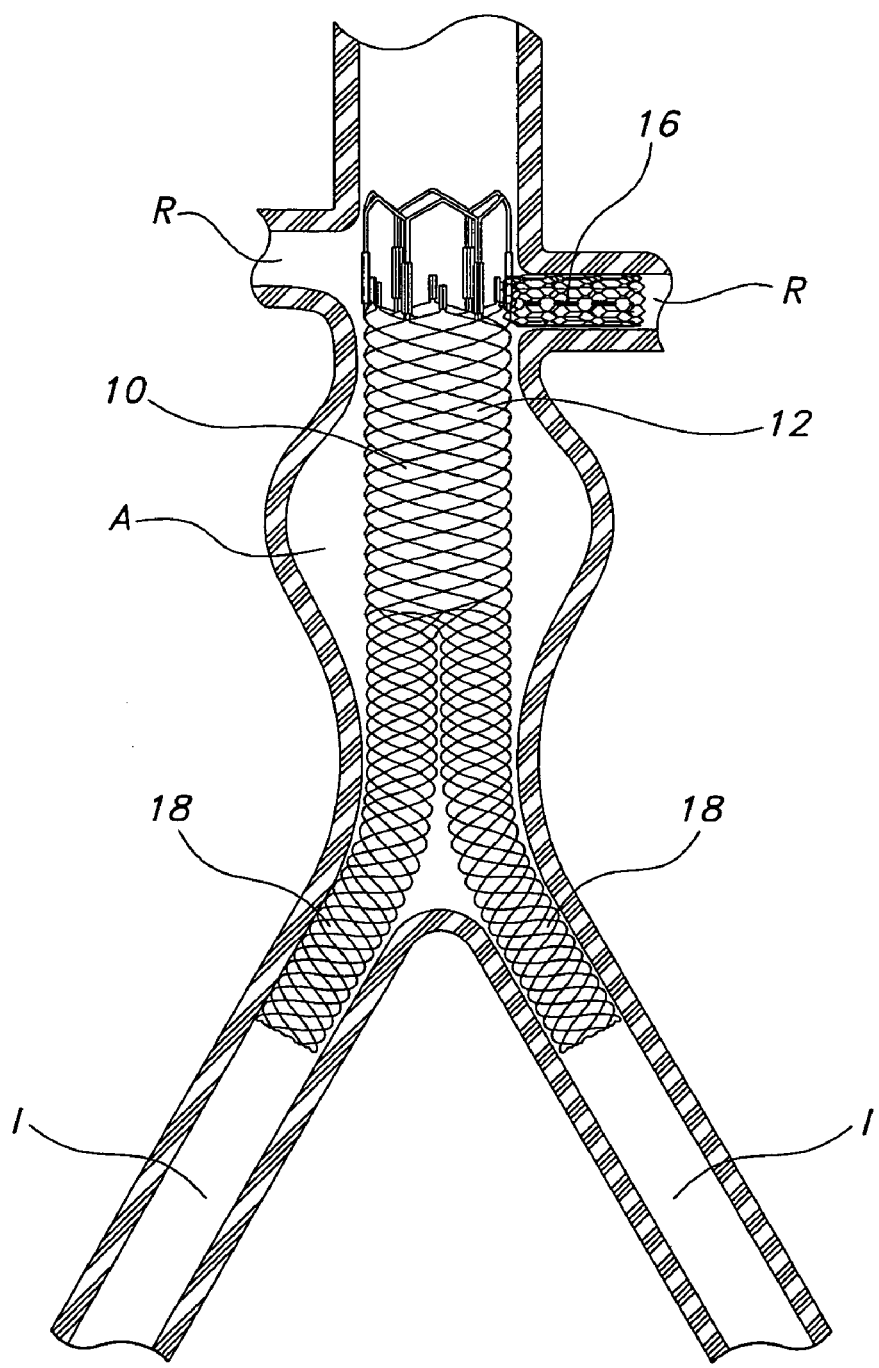
FIG. 1 illustrates an embodiment of a deployed endovascular prosthesis (shown without a graft) comprised of a main stent and an anchor stent pivotally connected to the main stent, showing the anchor stent placed within a renal artery.
Figure 2A:
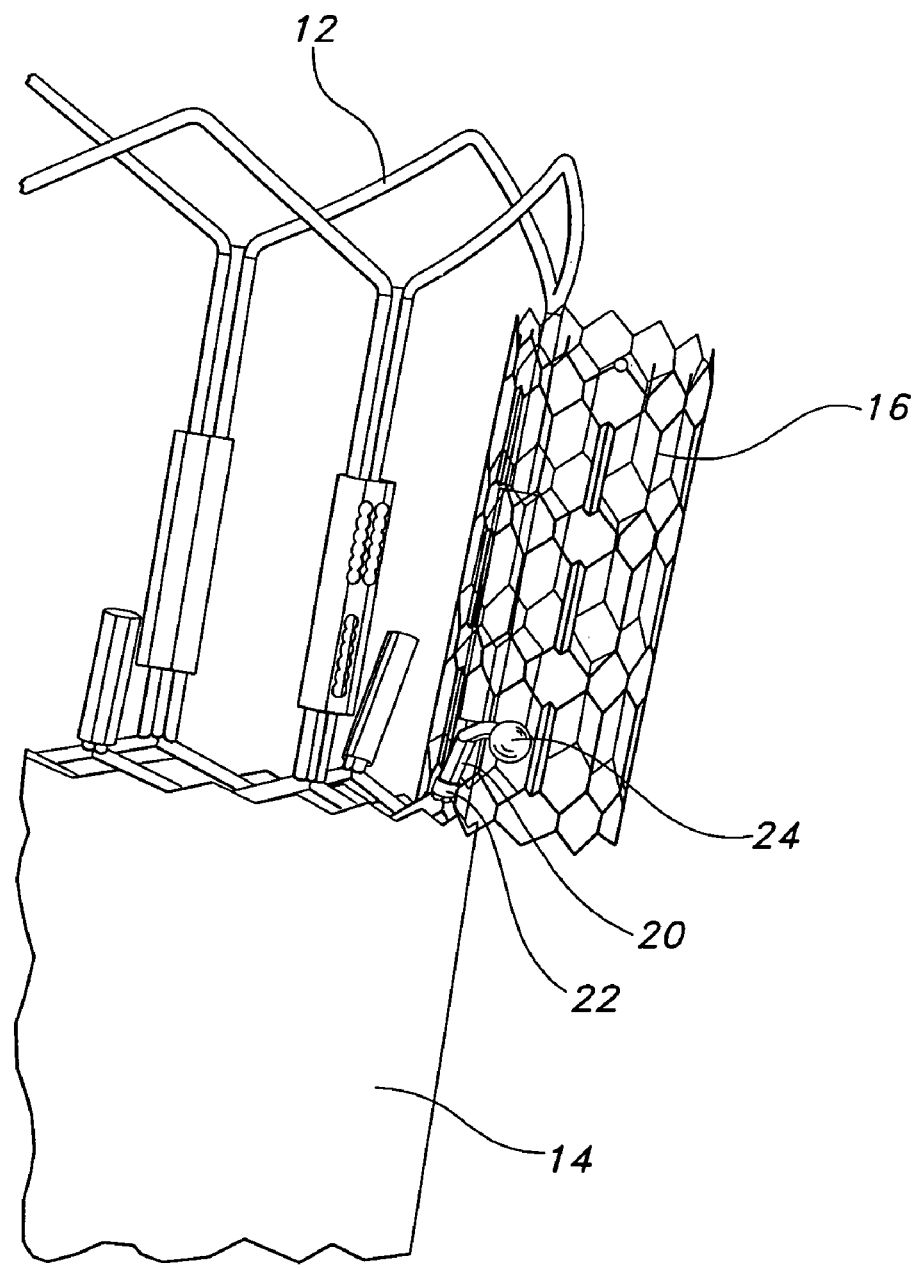
FIG. 2A is a detail view of the embodiment illustrated in FIG. 1, showing the anchor stent in a pre-deployment configuration.

Anchor stent 16 is oriented substantially coaxially to main stent 12 in a pre-deployment configuration (as illustrated in FIG. 2A), and substantially perpendicular to main stent 12 in a post-deployment configuration (as illustrated in FIGS. 1, 2B, 3, and 7A-8B).

FIG. 1 illustrates a deployed endovascular prosthesis 10 (shown without a graft 14, for clarity purposes) including a main stent 12 and an anchor stent 16 pivotally connected to main stent 12, showing anchor stent 16 placed within one of the renal arteries "R." Such placement of anchor stent 16 within renal artery "R" improves fixation of prosthesis 10 and resists migration. More specifically, due to changing vessel morphology, prosthesis 10 will typically be subjected to downward forces that may cause a conventional prosthesis to migrate distally (away from the heart). As represented in FIG. 1, axial movement of prosthesis 10 is limited by the fit of anchor stent 16 within renal artery "R."

The exemplary embodiment of main stent 12 illustrated in FIG. 1 includes a leg 18 extending within each iliac artery "I." The construction of main stent 12 may be of any type of self-expanding stent, and the construction of anchor stent 16 is preferably of any type of balloon-expandable stent. Main stent 12 may be formed from, for example, an expandable wire structure or a laser cut metallic structure. Similarly anchor stent 16 may be formed from, for example, an expandable wire structure or a laser cut metallic structure. The structures of main stent 12 and anchor stent 16 of this embodiment may be the same or they may be different, depending upon the specific application.

FIG. 2A is a detail view of prosthesis 10 showing anchor stent 16 in a pre-deployment configuration. More specifically, anchor stent 16 is oriented substantially coaxially to main stent 12 in the pre-deployment configuration. Graft 14 is represented covering a portion of main stent 12. In the pre-deployment configuration of prosthesis 10, main stent 12 and anchor stent 16 are each in a compressed state. However, for clarity purposes, main stent 12 and anchor stent 16 are each shown in an expanded state in FIG. 2A. The deployment method of prosthesis 10 will be described in detail below.

As shown in FIG. 2A, main stent 12 includes a substantially elbow-shaped shaft 20, and anchor stent 16 includes a collar 22 adapted to slide along shaft 20 to effect the pivotal connection. A stopper 24 is fixed to an end of shaft 20 to limit the movement of collar 22, and consequentially prevent anchor stent 16 from becoming detached from main stent 12.

The exemplary construction of shaft 20 includes two parallel cylindrical members. Shaft 20, however, is not limited to such an arrangement, and may include any number of members of any cross section suitable for pivotal cooperation with collar 22. The exemplary shape of stopper 24 is spherical. Stopper 24, however, is not limited to such a shape, and may be formed of any shape that offers the desired stopping feature.

Figure 2B:
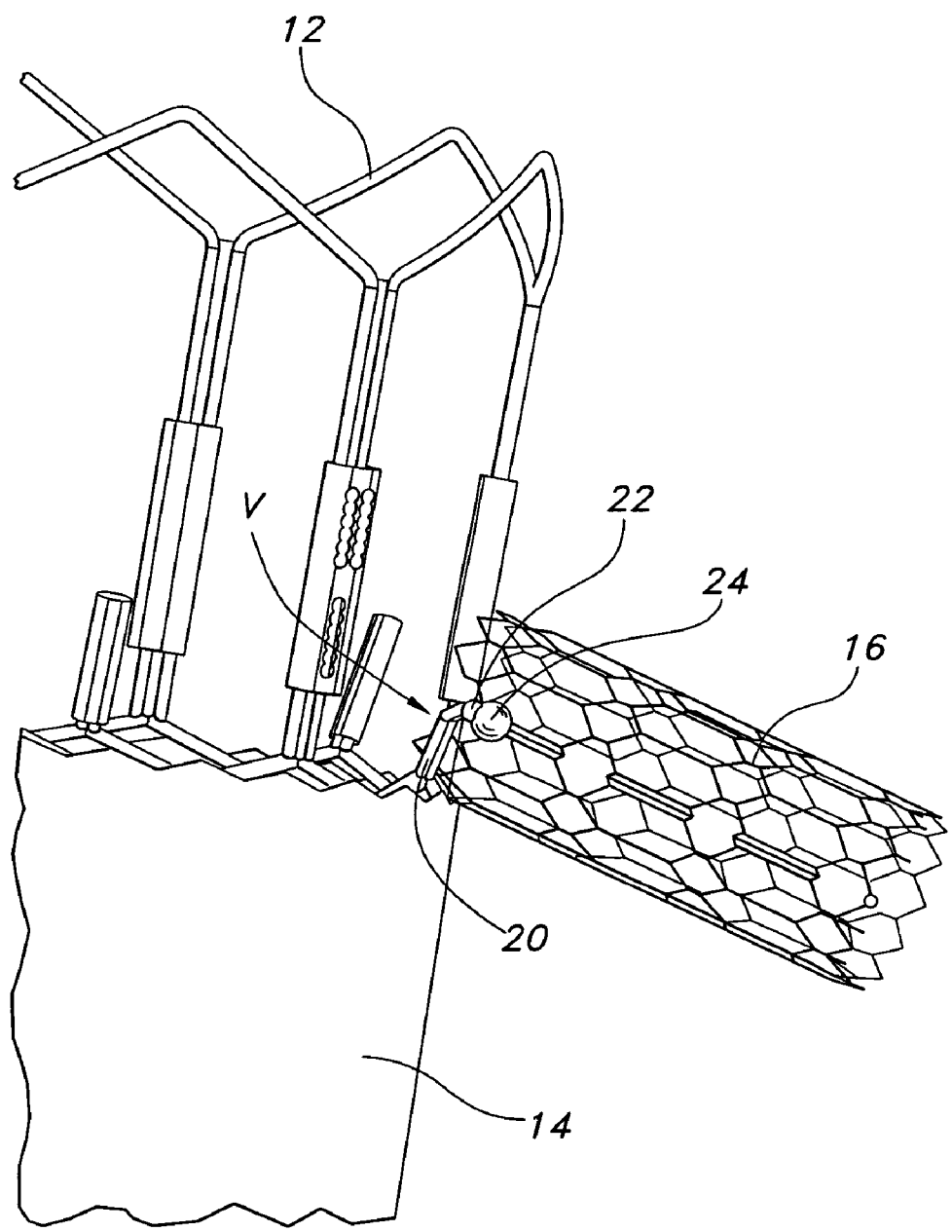
FIG. 2B is detail view similar to that of FIG. 2A, showing the anchor stent in a post-deployment configuration.

FIG. 2B is detail view similar to that of FIG. 2A, showing anchor stent 16 in a post-deployment configuration. More specifically, anchor stent 16 is oriented substantially perpendicular to main stent 12 in the post-deployment configuration (as illustrated in FIGS. 1, 2B, 3, and 7A-8B). In the fully post-deployment configuration of prosthesis 10, main stent 12 and anchor stent 16 are each in an expanded state. During the deployment method of prosthesis 10 (described in detail below) collar 22 slides along shaft 20 from the configuration illustrated in FIG. 2A to the configuration illustrated in FIG. 2B to effect the pivotal connection. As represented in FIG. 2B, stopper 24 limits the movement of collar 22, and consequentially prevents anchor stent 16 from becoming detached from main stent 12.

Figure 3:
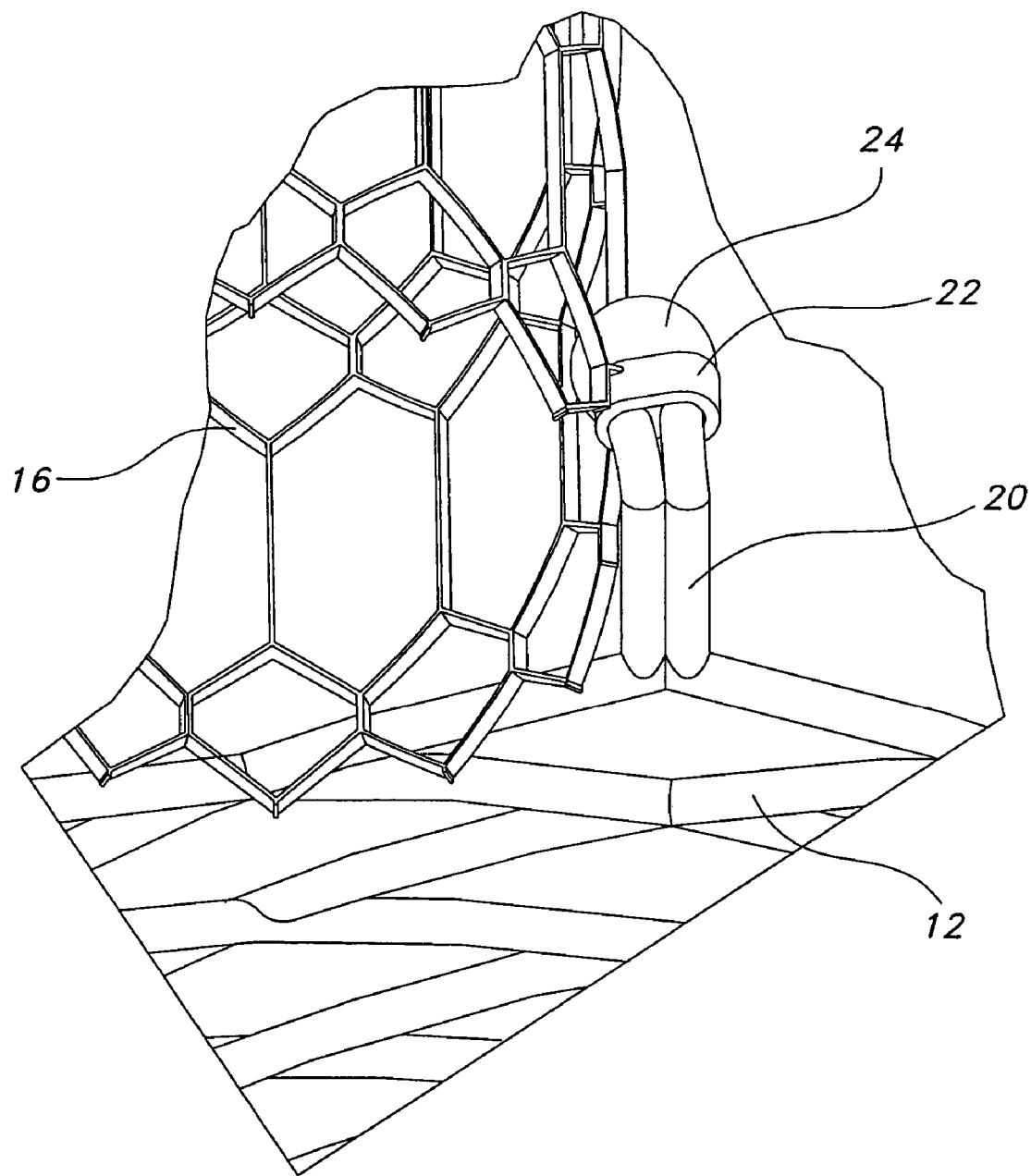
FIG. 3 is an expanded detail view of FIG. 2B in the direction of arrow "V," showing a collar of the anchor stent slideably mounted on a substantially elbow-shaped shaft of the main stent.

FIG. 3 is an expanded detail view of the same area shown in FIG. 2B, taken in the direction of arrow "V" in FIG. 2B. FIG. 3 shows collar 22 of anchor stent 16 slideably mounted on substantially elbow-shaped shaft 20 of main stent 12.

FIGS. 4A-4C show a delivery device 26 during various stages of deployment of prosthesis 10. The deployment method itself will be described in detail below with reference to FIGS. 5A-8B.

FIG. 4A is a representation of delivery device 26 comprised of a tip 28 and a sheath 30 for deployment of endovascular prosthesis 10. Sheath 30 contains prosthesis 10 (not shown), keeping self-expandable main stent 12 (not shown) in its compressed state. Delivery device 26 includes a main stent guide wire port 32, an anchor stent guide wire port 34, and a balloon inflation port 36. Tip 28 of delivery device 26 includes a main stent guide wire lumen 38 in the form of an axial through-hole, and an anchor stent guide wire lumen 40 in the form of a surface groove.

FIG. 4B shows delivery device 26 illustrated in FIG. 4A during an early stage of deployment with anchor stent 16 in a pre-deployment configuration. As in FIG. 2A, anchor stent 16 is oriented substantially coaxially to main stent 12. Unlike FIG. 2A, however, main stent 12 and anchor stent 16 are each represented in a compressed state in FIG. 4B. Sheath 30 is partially withdrawn to partially release main stent 12 and anchor stent 16 of endovascular prosthesis 10. Balloon-expandable anchor stent 16 is in its compressed state around a balloon catheter 42. FIG. 4B further illustrates the main stent guide wire 44 extending through main stent 12 and main stent guide wire lumen 38, and the anchor stent guide wire 46 extending through anchor stent 16.

FIG. 4C shows delivery device 26 during a later stage of deployment with anchor stent 16 in a post-deployment configuration. As in FIG. 2B, anchor stent 16 is oriented substantially perpendicular to main stent 12. Unlike FIG. 2B, however, main stent 12 and anchor stent 16 are each represented in a compressed state in FIG. 4C. It is not until prosthesis 10 is fully deployed that main stent 12 and anchor stent 16 are each in an expanded state (post-deployment configuration) as illustrated in FIG. 2B. As illustrated in FIG. 4C, sheath 30 contains prosthesis 10, keeping self-expandable main stent 12 in its compressed state. Sheath 30 is further withdrawn and anchor stent 16 (still in its compressed state around balloon catheter 42) is fully released from sheath 30.

The deployment method of prosthesis 10 will be described in detail below with reference to FIGS. 5A-8B.

Figure 5A:
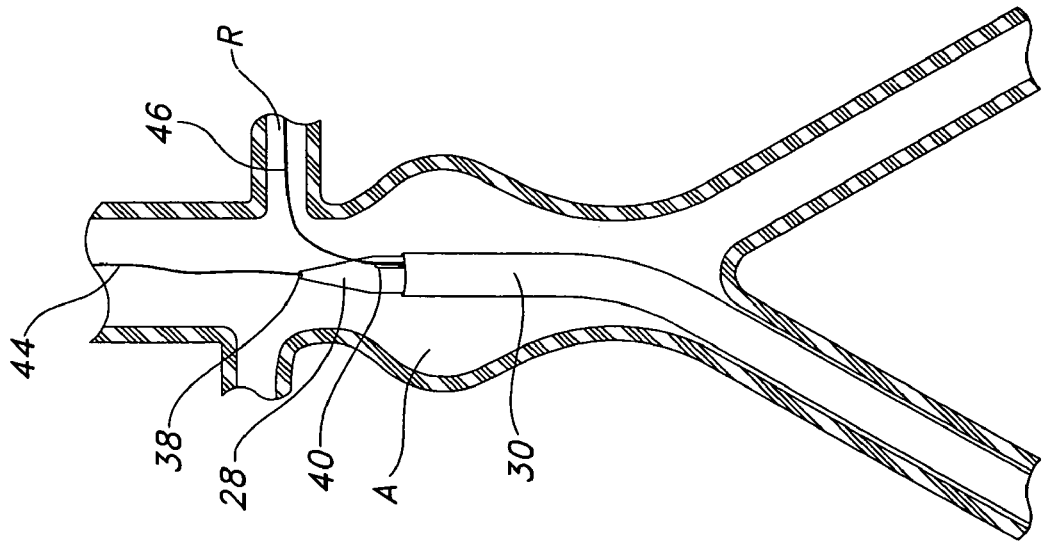
FIG. 5A illustrates a guide wire for the anchor stent advanced from an iliac artery through a renal artery.
Figure 5B:
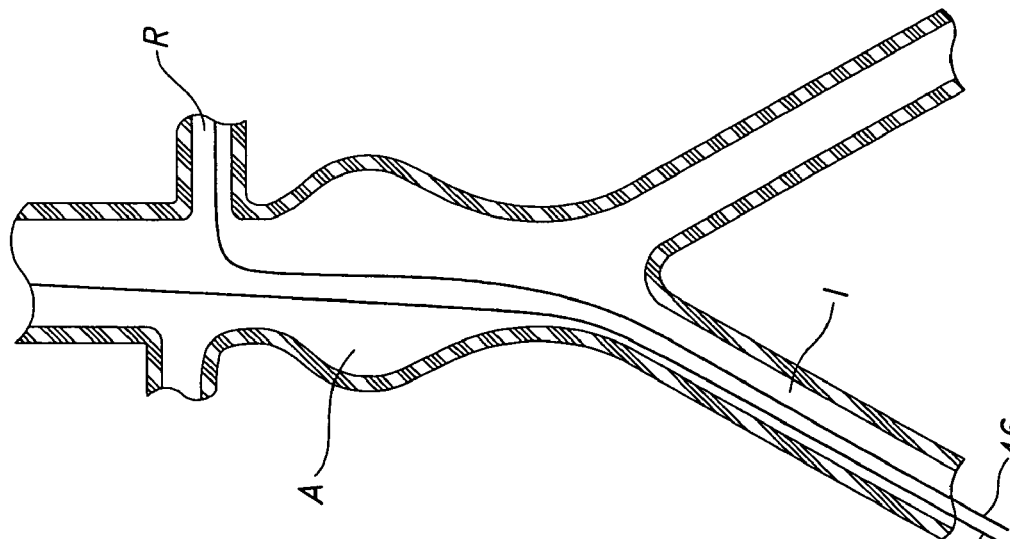
FIG. 5B illustrates a guide wire for the main stent advanced from the iliac artery through the aorta.
Figure 5C:
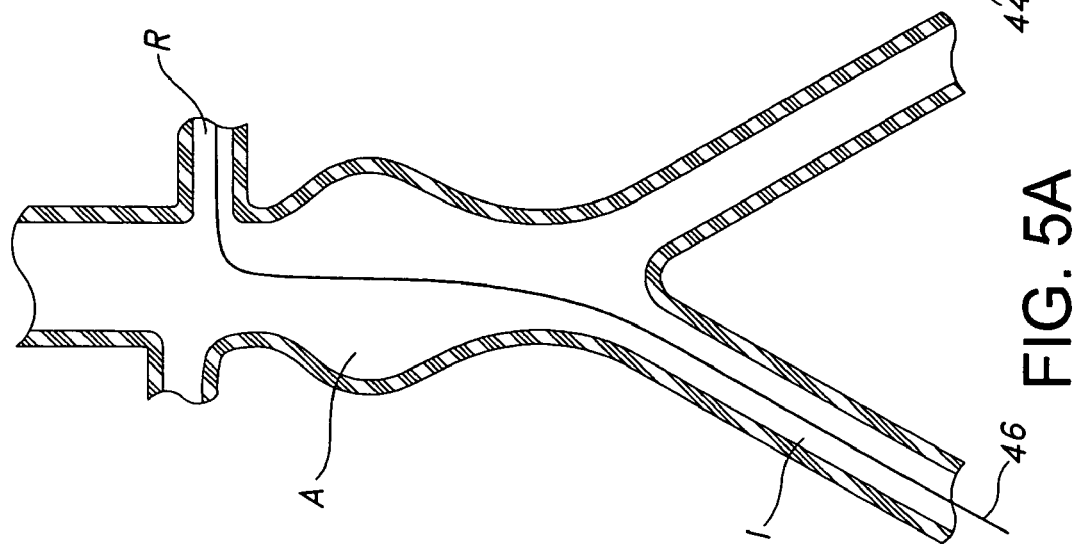
FIG. 5C shows the delivery device represented in FIG. 4A advanced over the guide wires illustrated in FIGS. 5A and 5B.

FIG. 5A illustrates that a first guide wire (anchor stent guide wire 46) is advanced from an iliac artery "I" through a renal artery "R." FIG. 5B illustrates that a second guide wire (main stent guide wire 44) is advanced from the same iliac artery "I" through the aorta "A." FIG. 5C shows that delivery device 26 is advanced over guide wires 44 and 46. Main stent guide wire 44 extends through main stent 12 (not shown) and main stent guide wire lumen 38, and anchor stent guide wire 46 extends through anchor stent 16 (not shown) and anchor stent guide wire lumen 40.

Figure 6C:
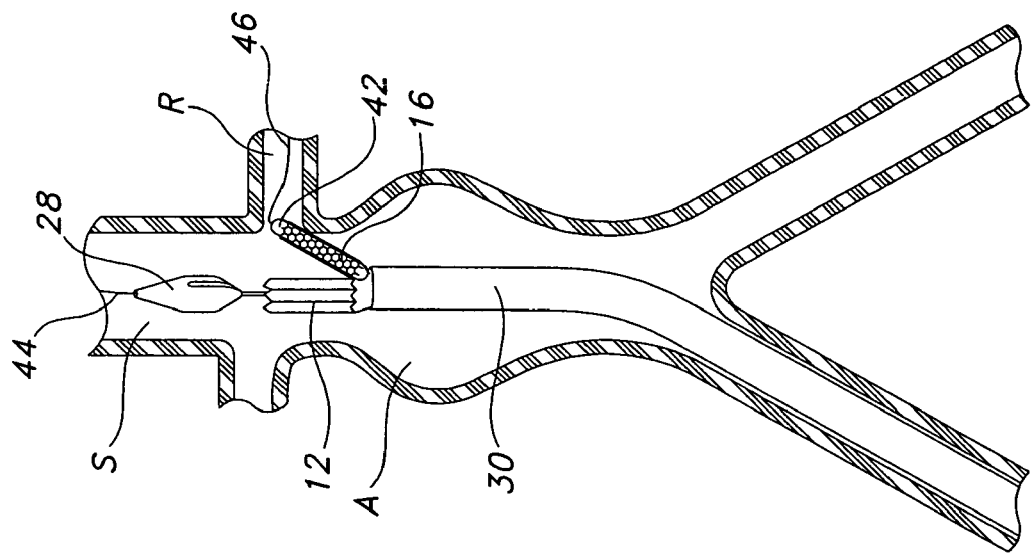
FIG. 6C is a view similar to that of FIG. 6B, showing the anchor stent advanced toward the renal artery.
Figure 6B:
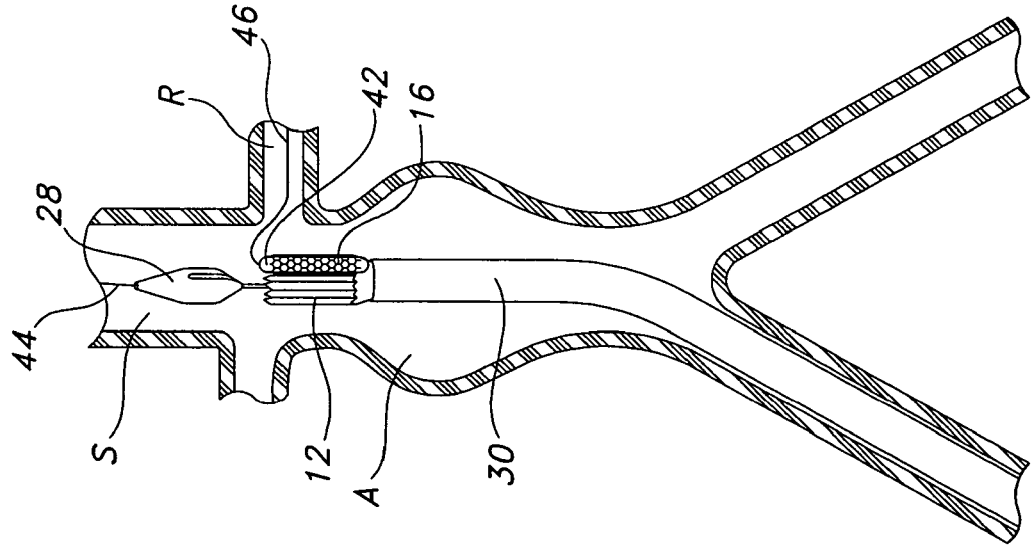
FIG. 6B is a view similar to that of FIG. 6A, showing the sheath further withdrawn and the anchor stent (in a compressed state around a balloon catheter) fully released from the sheath.
Figure 6A:
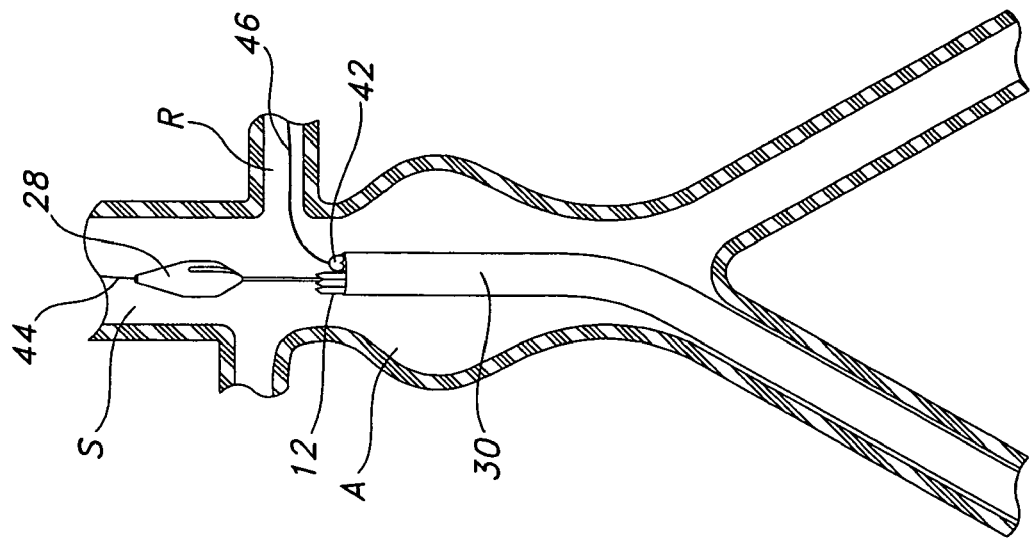
FIG. 6A shows the cone of the delivery device represented in FIG. 4A advanced to the supra-renal region, and the sheath partially withdrawn to partially release the main stent and the anchor stent of the endovascular prosthesis illustrated in FIG. 1.

FIG. 6A shows that cone 28 of delivery device 26 is advanced to the supra-renal region "S." Sheath 30 is partially withdrawn to partially release main stent 12 and anchor stent 16 of endovascular prosthesis 10. This stage of the deployment method is similar to that described above with reference to FIG. 4B.

FIG. 6B shows that sheath 30 is further withdrawn and anchor stent 16 (in a compressed state around balloon catheter 42) is fully released from sheath 30. At this stage, main stent 12 is partially deployed, yet it may be repositioned as desired.

FIG. 6C shows that anchor stent 16 is advanced toward the ostium of renal artery "R." As described above with reference to FIG. 2B, collar 22 (not shown) of anchor stent 16 slides along shaft 20 (not shown) of main stent 12 from the configuration illustrated in FIG. 2A to the configuration illustrated in FIG. 2B to effect the pivotal connection that facilitates the advancement of anchor stent 16 toward renal artery "R."

Figure 7C:
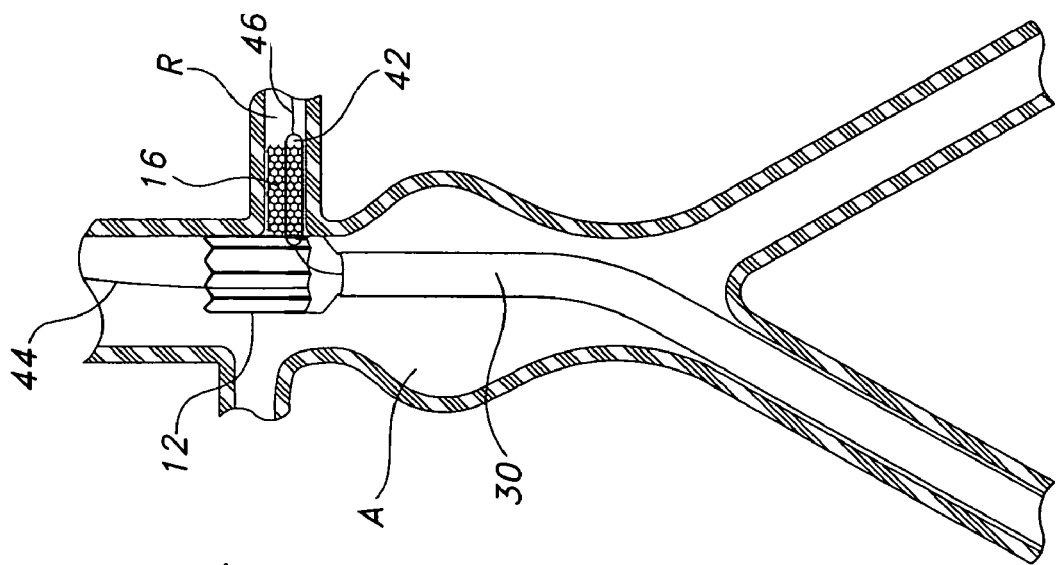
FIG. 7C is view similar to that of FIG. 7B, showing the balloon deflated.
Figure 7B:
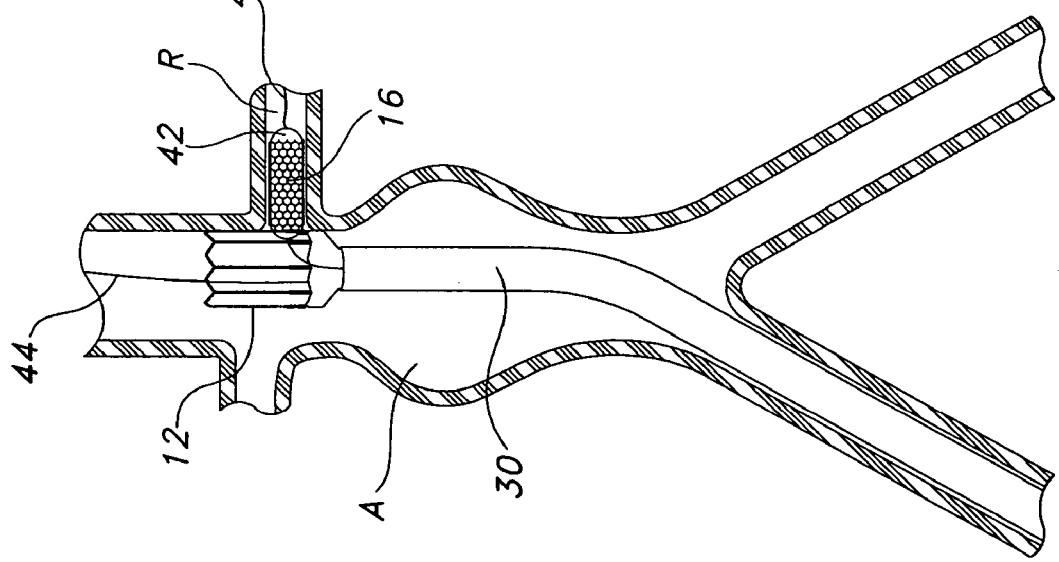
FIG. 7B is a view similar to that of FIG. 7A, showing the balloon inflated and the anchor stent in an expanded state.
Figure 7A:
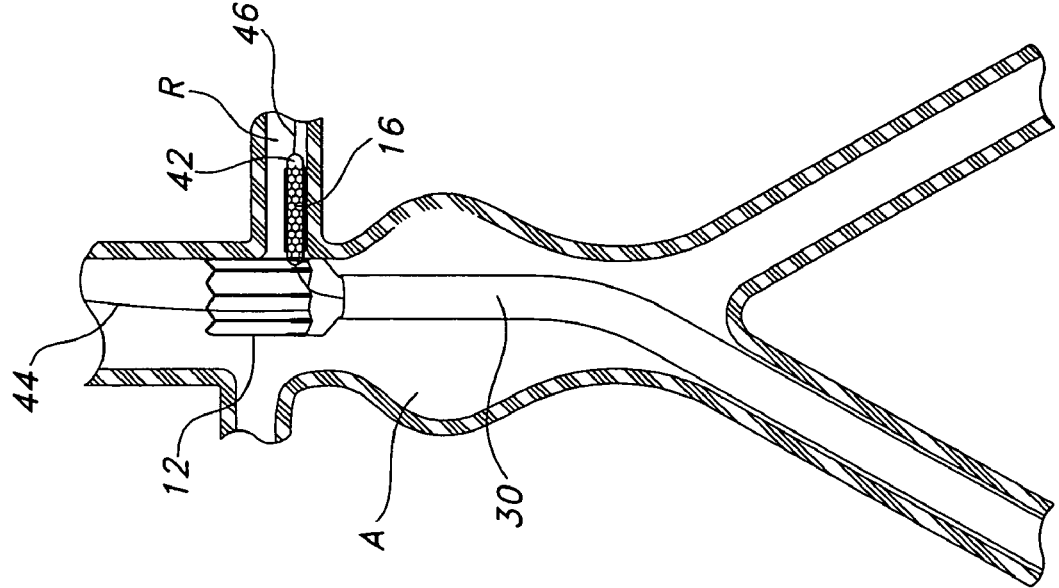
FIG. 7A shows the anchor stent (in a compressed state around the balloon catheter) positioned within the renal artery.

For simplicity purposes, tip 28 is not represented in FIGS. 7A-8A. FIG. 7A shows anchor stent 16 (in a compressed state around balloon catheter 42) is positioned within renal artery "R." This stage of the deployment method is similar to that described above with reference to FIG. 4C.

FIG. 7B shows that balloon 42 is inflated utilizing balloon inflation port 36 of delivery device 26 (represented in FIGS. 4A-4C) and anchor stent 16 is expanded to its expanded state. FIG. 7C shows that balloon 42 is deflated, leaving anchor stent 16 in its expanded state within renal artery "R."

Figure 8A:
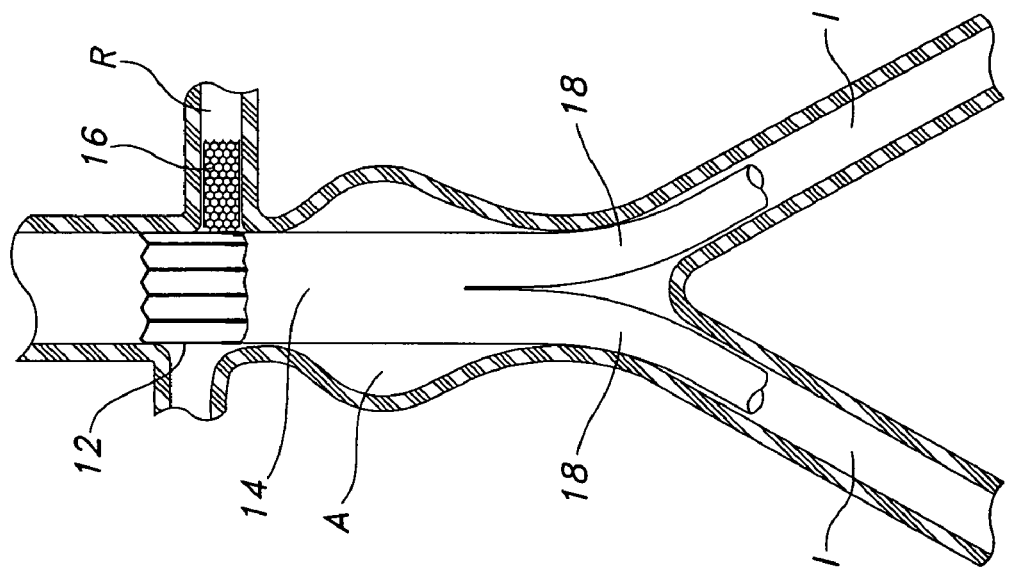
FIG. 8A shows the sheath further withdrawn and the proximal portion of the main stent fully released and expanded.

FIG. 8A shows sheath 30 further withdrawn and the proximal portion (closest to the heart) of main stent 12 fully released and expanded. Balloon catheter 42 has been removed.

Figure 8B:
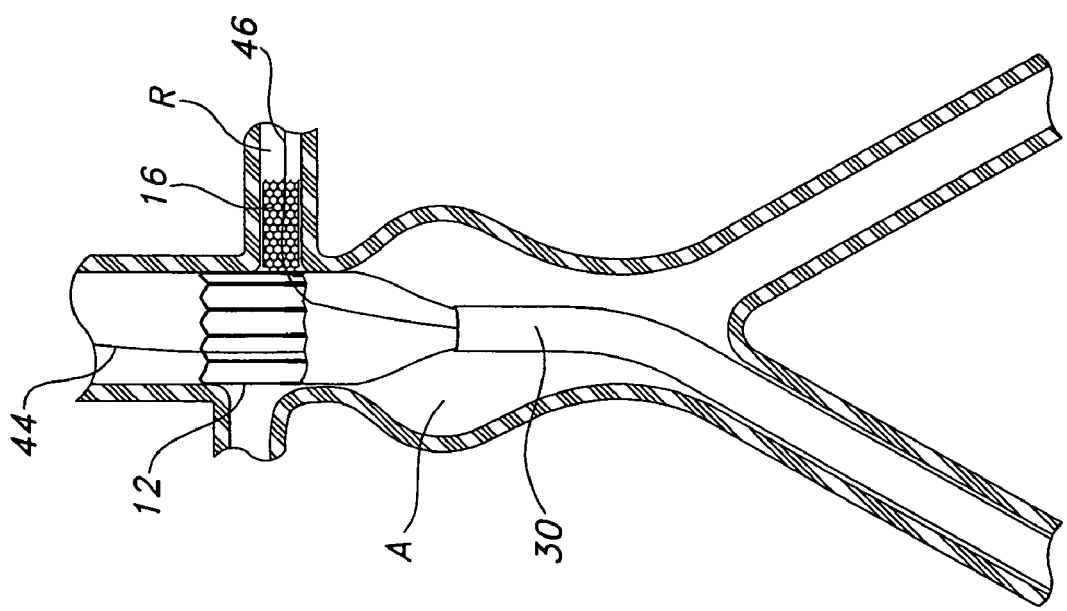
FIG. 8B illustrates the endovascular prosthesis (shown with a graft) deployed with the sheath fully withdrawn and the guide wires removed.

FIG. 8B shows that guide wires 44 and 46 and tip 28 are removed. Sheath 30 is fully withdrawn and main stent 12 is fully released and expanded within the aorta "A." In other words, FIG. 8 illustrates endovascular prosthesis 10 (shown with graft 14) fully deployed. Legs 18 of main stent 12 are deployed within iliac arteries "I" in a conventional manner such as, for example, that disclosed in U.S. Pat. No. 6,773,453 to Ravenscroft, or by extension of a short leg with a mating stent-graft introduced through iliac "I" on the right as shown in FIG. 8B.

Figure 9:
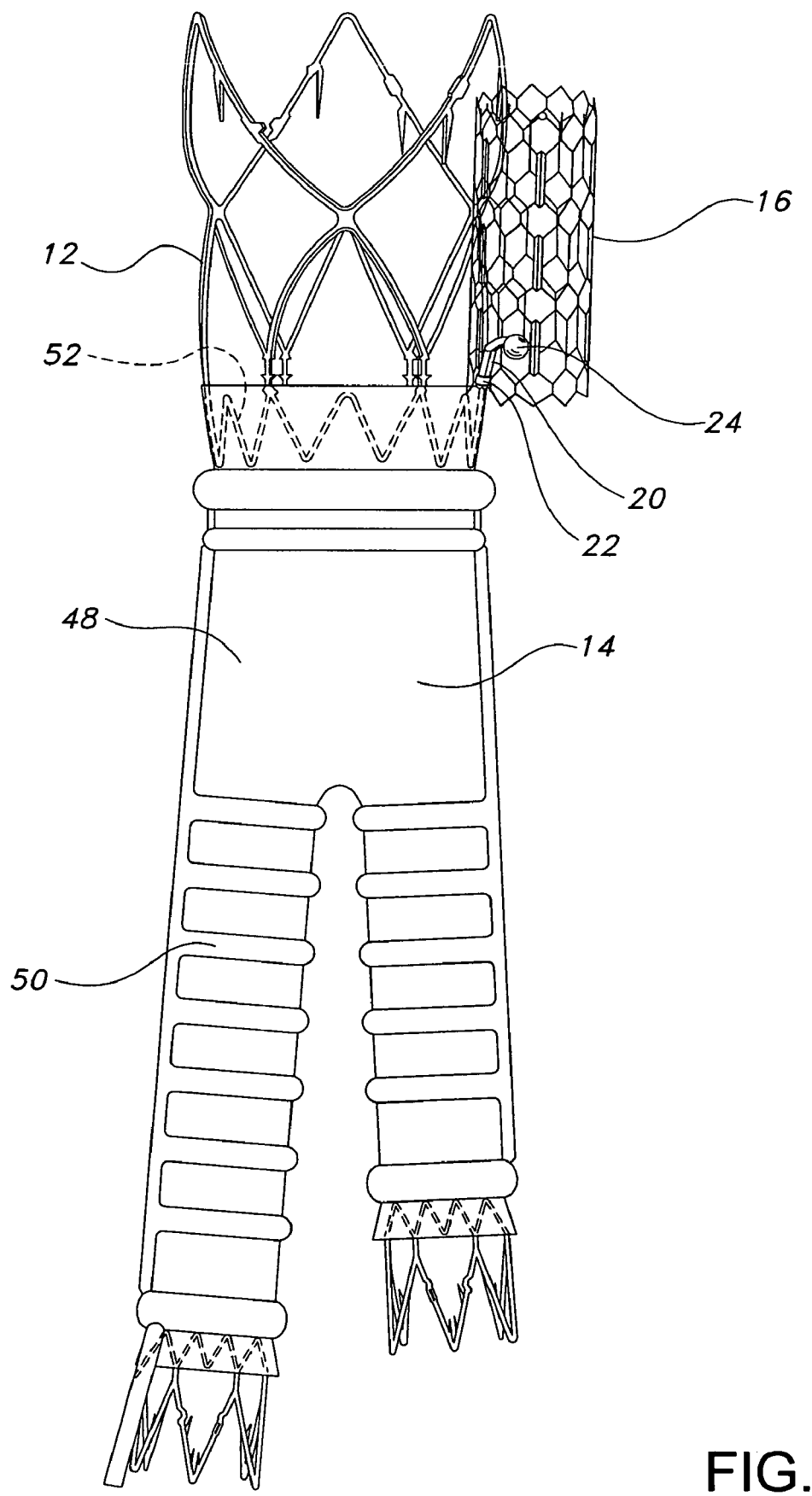
FIG. 9 illustrates another embodiment of an endovascular prosthesis (shown with a graft) comprised of a main stent and an anchor stent pivotally connected to the main stent, showing the anchor stent in a pre-deployment configuration.

FIG. 9 illustrates another embodiment of the endovascular prosthesis 10 (shown with a graft 14) including a main stent 12 and an anchor stent 16 pivotally connected to the main stent 12, showing anchor stent 16 in a pre-deployment configuration. The configuration and deployment method of this exemplary embodiment are essentially the same as those of prosthesis 10 described above with reference to FIGS. 1-8B, with some notable differences. Main stent 12 illustrated in FIG. 9 is formed from a tubular member 48 rigidified by a network of channels 50 inflated by a filler material. Such a prosthesis is described, for example, in U.S. Pat. No. 5,871,537 to Holman et al., and U.S. Patent Application Publication No. US 2003/0120331 to Chobotov et al. Main stent 12 also includes a connecting ring 52, connected to an upper wire frame or laser cut frame landing section, which is mated with anchor stent 16 as in the embodiment illustrated in FIG. 1.

Anchor stent 16, as illustrated in FIG. 9, may be formed from an expandable wire structure or a laser cut metallic structure. Alternatively, anchor stent 16 may also be formed from a tubular member rigidified by a network of channels inflated by a filler material. The structures of main stent 12 and anchor stent 16 of this embodiment may be the same or they may be different, depending upon the specific application.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

What is claimed is:

1. An endoluminal prosthesis for treatment of a condition in a main lumen in the vicinity of a branch lumen, said prosthesis adapted to resist migration, said prosthesis comprising:
   a substantially tubular main stent adapted for placement in the main lumen, the main stent comprising a plurality of main stent members;
   a substantially elbow-shaped shaft formed from a plurality of parallel main stent members in contact with each other, the shaft having a free end comprising a stopper;
   a substantially tubular anchor stent pivotally connected to said main stent and adapted for placement in the branch lumen; and
   a collar coupled to the anchor stent, the collar being slidingly coupled to the shaft to effect the pivotal connection.

2. The prosthesis of claim 1, wherein said anchor stent is adapted to be oriented substantially perpendicular to said main stent in a post-deployment configuration.

3. The prosthesis of claim 1, wherein said stopper limits movement of said collar at the free end of the shaft.

4. The prosthesis of claim 1, wherein said main stent is self-expandable.

5. The prosthesis of claim 1, wherein said anchor stent is balloon-expandable.

6. The prosthesis of claim 1, wherein said main stent is a bifurcated stent.

7. The prosthesis of claim 1, wherein said main stent comprises an expandable wire structure.

8. The prosthesis of claim 1, wherein said main stent comprises a laser cut metallic structure.

9. The prosthesis of claim 1, wherein said main stent comprises a tubular member rigidified by a network of channels inflated by a filler material.

10. The prosthesis of claim 1, wherein said anchor stent comprises an expandable wire structure.

11. The prosthesis of claim 1, wherein said anchor stent comprises a laser cut metallic structure.

12. The prosthesis of claim 1, wherein said anchor stent comprises a tubular member rigidified by a network of channels inflated by a filler material.

13. A method of endoluminally deploying an endovascular prosthesis for treatment of an abdominal aortic aneurysm, the prosthesis being adapted to resist migration and comprising:
   a main stent adapted for placement below the renal arteries;
   a substantially elbow-shaped shaft having a fixed end coupled to and extending outwardly from the main stent, the shaft having a free end comprising a stopper;
   an anchor stent adapted for placement in a renal artery and pivotally connected to the main stent; and
   a collar coupled to the anchor stent, the collar being slidingly coupled to the shaft to effect the pivotal connection, said method comprising the steps of:
   advancing a first guide wire for the anchor stent through the renal artery;
   advancing a second guide wire for the main stent through the aorta;
   advancing the main stent over the second guide wire to endoluminally position the prosthesis at a preselected position in the aorta;
   pivoting and advancing the anchor stent over the first guide wire into position within the renal artery by sliding the collar along the shaft;
   expanding the anchor stent within the renal artery; and
   expanding the main stent within the aorta.

14. The method of claim 13, wherein said step of expanding the anchor stent within the renal artery further comprises the steps of:
   introducing a filler material into a network of channels within the anchor stent;
   inflating the anchor stent via the filler material; and
   rigidifying the anchor stent.

15. The method of claim 13, wherein said step of expanding the main stent within the aorta further comprises the steps of:
   introducing a filler material into a network of channels within the main stent;
   inflating the main stent via the filler material; and
   rigidifying the main stent.

* * * * *